US012702720B2

(12) United States Patent
Zhou et al.

(10) Patent No.: US 12,702,720 B2
(45) Date of Patent: Aug. 11, 2026

(54) GENOMIC INSULATOR ELEMENT EXHIBITING ENHANCER BLOCKING ACTIVITIES IN LYMPHOCYTES AND USES THEREOF

(71) Applicant: ST. JUDE CHILDREN'S RESEARCH HOSPITAL, INC., Memphis, TN (US)

(72) Inventors: Sheng Zhou, Memphis, TN (US); Brian Sorrentino, Memphis, TN (US); Yong Cheng, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 814 days.

(21) Appl. No.: 17/924,469

(22) PCT Filed: May 7, 2021

(86) PCT No.: PCT/US2021/031210

§ 371 (c)(1),
(2) Date: Nov. 10, 2022

(87) PCT Pub. No.: WO2021/231192

PCT Pub. Date: Nov. 18, 2021

(65) Prior Publication Data

US 2023/0181762 A1 Jun. 15, 2023

Related U.S. Application Data

(60) Provisional application No. 63/024,651, filed on May 14, 2020.

(51) Int. Cl.
*A61K 48/00* (2006.01)
*C12N 15/86* (2006.01)

(52) U.S. Cl.
CPC .......... *A61K 48/0008* (2013.01); *C12N 15/86* (2013.01); *C12N 2740/15043* (2013.01); *C12N 2830/40* (2013.01); *C12N 2830/48* (2013.01)

(58) Field of Classification Search
None
See application file for complete search history.

(56) References Cited

U.S. PATENT DOCUMENTS

2003/0211581 A1 11/2003 Herr et al.
2007/0031847 A1* 2/2007 Cargill ................ C12Q 1/6883 536/23.2
2016/0032318 A1 2/2016 Molina et al.
2017/0175136 A1 6/2017 Stamatoyannopoulos et al.
2019/0309291 A1 10/2019 Lee et al.

FOREIGN PATENT DOCUMENTS

WO 2001092483 A1 12/2001
WO 2009016206 A1 2/2009
WO 2015138852 A1 9/2015

OTHER PUBLICATIONS

Al-Rubeai et al., Viral Vectors for Gene Therapy, 2011, Springer, Chapter 8, p. 183, Abstract (Year: 2011).*
Kuo et al., Gene Therapy for the Treatment of Primary Immune Deficiencies, 2016, Author Manuscript, Curr Allergy Asthma Rep. vol. 16, p. 1-12 (Year: 2016).*
International Preliminary Report on Patentability in PCT/US2021/031210 dated Nov. 24, 2022.
International Search Report and Written Opinion in PCT/US2021/031210 dated Jun. 14, 2022.

* cited by examiner

*Primary Examiner* — Tracy Vivlemore
*Assistant Examiner* — Hanna Marie Thueson
(74) *Attorney, Agent, or Firm* — Licata & Tyrrell P.C.; Jane Massey Licata

(57) ABSTRACT

A construct including a genomic insulator element that exhibits strong enhancer blocking activities in T lymphocytes is provided as are host cells, pharmaceutical compositions and methods of using the construct in the treatment of disease, in particular a disease to be treated with a retroviral vector-modified T lymphocyte.

11 Claims, No Drawings

Specification includes a Sequence Listing.

SEQUENCE LISTING

```
<160> NUMBER OF SEQ ID NOS: 40

<210> SEQ ID NO 1
<211> LENGTH: 19
<212> TYPE: DNA
<213> ORGANISM: Homo sapiens

<400> SEQUENCE: 1

cactgccctc cagtggcca                                                    19


<210> SEQ ID NO 2
<211> LENGTH: 19
<212> TYPE: DNA
<213> ORGANISM: Homo sapiens

<400> SEQUENCE: 2

cagcgccacc tgcaggcca                                                    19


<210> SEQ ID NO 3
<211> LENGTH: 19
<212> TYPE: DNA
<213> ORGANISM: Homo sapiens

<400> SEQUENCE: 3

cttccagcag gaggaggca                                                    19


<210> SEQ ID NO 4
```

<211> LENGTH: 19
<212> TYPE: DNA
<213> ORGANISM: Homo sapiens

<400> SEQUENCE: 4
tggccgctag agggcacgc 19

<210> SEQ ID NO 5
<211> LENGTH: 19
<212> TYPE: DNA
<213> ORGANISM: Homo sapiens

<400> SEQUENCE: 5
aagcaccatc tactggtct 19

<210> SEQ ID NO 6
<211> LENGTH: 19
<212> TYPE: DNA
<213> ORGANISM: Homo sapiens

<400> SEQUENCE: 6
ctgccgccag atggcgctc 19

<210> SEQ ID NO 7
<211> LENGTH: 19
<212> TYPE: DNA
<213> ORGANISM: Homo sapiens

<400> SEQUENCE: 7
tcagcactag atggcaccc 19

<210> SEQ ID NO 8
<211> LENGTH: 19
<212> TYPE: DNA
<213> ORGANISM: Homo sapiens

<400> SEQUENCE: 8
gagtgacacc tagtggccc 19

<210> SEQ ID NO 9
<211> LENGTH: 19
<212> TYPE: DNA
<213> ORGANISM: Homo sapiens

<400> SEQUENCE: 9
cagcgccatc tggcggccg 19

<210> SEQ ID NO 10
<211> LENGTH: 19
<212> TYPE: DNA
<213> ORGANISM: Homo sapiens

<400> SEQUENCE: 10
tcgccagtag ggggcgcaa 19

<210> SEQ ID NO 11
<211> LENGTH: 19
<212> TYPE: DNA
<213> ORGANISM: Homo sapiens

<400> SEQUENCE: 11
tgctgccccc tggtggcca 19

<210> SEQ ID NO 12
<211> LENGTH: 19
<212> TYPE: DNA
<213> ORGANISM: Homo sapiens

<400> SEQUENCE: 12
tgctgctccc ttatggcca 19

<210> SEQ ID NO 13
<211> LENGTH: 19
<212> TYPE: DNA
<213> ORGANISM: Homo sapiens

<400> SEQUENCE: 13
aggccaccag atggcattg 19

<210> SEQ ID NO 14
<211> LENGTH: 19
<212> TYPE: DNA
<213> ORGANISM: Homo sapiens

<400> SEQUENCE: 14
ctgccacgag ggggcggca 19

<210> SEQ ID NO 15
<211> LENGTH: 19
<212> TYPE: DNA
<213> ORGANISM: Homo sapiens

<400> SEQUENCE: 15
ttgcgccccc tgctggcga 19

<210> SEQ ID NO 16
<211> LENGTH: 19
<212> TYPE: DNA
<213> ORGANISM: Homo sapiens

<400> SEQUENCE: 16
cgtcgccacc ttctggtaa 19

<210> SEQ ID NO 17
<211> LENGTH: 19
<212> TYPE: DNA
<213> ORGANISM: Homo sapiens

<400> SEQUENCE: 17
cagtgccctc tggtggtag 19

<210> SEQ ID NO 18
<211> LENGTH: 19
<212> TYPE: DNA
<213> ORGANISM: Homo sapiens

<400> SEQUENCE: 18
ttatgccccc tgcaggaca 19

<210> SEQ ID NO 19
<211> LENGTH: 19
<212> TYPE: DNA
<213> ORGANISM: Homo sapiens

<400> SEQUENCE: 19
cgcccagaag gtggcggca 19

<210> SEQ ID NO 20
<211> LENGTH: 19
<212> TYPE: DNA
<213> ORGANISM: Homo sapiens

<400> SEQUENCE: 20
cactgccccc tagtggacc 19

<210> SEQ ID NO 21
<211> LENGTH: 463
<212> TYPE: DNA
<213> ORGANISM: Homo sapiens

<400> SEQUENCE: 21
gcgaggggag acacaggggc cggggctgcg gcggctgagc tccctgggcg gctcggaacg 60
caaggggccg gcgagccgac gctgctgcag gaggctgcgg cgtggggcga ggttctcgct 120
acggcttcgt tcccgtcctc ccgcggccgc tctcccccgg aagccctcgg aggcagcacg 180
atggacgtgg ccacactgcc ctccagtggc cagctcgccg aacaacacgt ctgggcccct 240
tttgggggtc tgggtgacgt gtccaccctc tctctgccct ttgctacatt tgaaggtggg 300
gtttgctcat ccatggttcc tcttacaggt caccaaagct gccacagtgc acactcaccc 360
aacagcaggg gatttgccgc cttcggtggt tctcaaactt cagtgtgcac aggaatcccc 420
ccttggacag ttctttcaaa cccggattgc tgggtccccc aac 463

<210> SEQ ID NO 22
<211> LENGTH: 394
<212> TYPE: DNA
<213> ORGANISM: Homo sapiens

<400> SEQUENCE: 22
ctgacccgta cccctgaacc gagcaagcct aggagcaggt gcgccggcgg cgctgtgaag 60
cggcactcat gacaggcagg ctgggcaccg ccacccccgaa acctccgagg gaggaccagc 120
cagcccaggt tggcgctgga gctgcagcgc cacctgcagg ccaaggagtc tttttctggg 180
aggctggagc tgcagcgcca cctgcaggcc aaggagtctt tttctgggag gctggagctg 240
cagcgccacc tgcaggccaa ggagtctttt tctgggaggc tggagctgca gatgcagtga 300
agtcacaggt tccgtgatgt cacaggtggg caggcgcact ggtctgtaac ggattggctt 360
ggccttaccc acgaggcttt gcggtggctg ttgg 394

<210> SEQ ID NO 23
<211> LENGTH: 589
<212> TYPE: DNA
<213> ORGANISM: Homo sapiens

<400> SEQUENCE: 23
gtgctgggga ggcagtgagg gctgaaaaag gccagggagg gaagagggga ggggagggaa 60
gcagtaaggt ggagcaggcc tggccagaaa gagccaggaa taaagcttcc tctagtgtct 120
tgagcctagg ccttcttcct tcagtggaac ctccctttgc ttccagcagg aggaggcagg 180
agaacctagg tctacaggct ttcctgccat ggtcttaggg actggataag gcccaccttc 240
aggtttgggc accttccaag tggcctgtga accccctaaag ggcaagagct ggggtacgat 300
gtccctttgc cccagtgacc cagaagcagg ttcaatctgt gcctcacagc accaccgtgt 360
ggcttcccct gggactgcag ccgcctaact gggtgtggcc ctgagtgtgg agctggctac 420
tacaattcct ttgaatctgt cgatctaaaa taagtgaaaa ggccagaacc tagtttagag 480

```
agagtttatt caagcacaca tgttgaggac aggcctaccc aggaagcaca aattccaaag    540

aatggaagtc agccttcctg ttcgaaatgt aggagcttgg gatcattta                589


<210> SEQ ID NO 24
<211> LENGTH: 405
<212> TYPE: DNA
<213> ORGANISM: Homo sapiens

<400> SEQUENCE: 24

tcccaaggct gctgcctgca tgccactccg tgaggaagtt gaaatacatg gtctctaaga     60

ttccttccag ctcttcacct catgagacat ataaatcaag taacattcgt tattgtgatt    120

agaaaagctg catttacaca cgttagccac tagatgggga cgtgcgattg ttacaatgct    180

gaaggtttcc cgtatttctt tattttttat ttggccgcta gagggcacgc ctgcactgca    240

cttaaagttg actactttca aggaaagaca aaggaattct tggatttctc cattttcctc    300

atcacctgtg cttatcagag aattccaggg gcaagctacc ctttccaatt catcactaac    360

ttataaacaa aattctaagg agtaaggaat gcttcttact tactt                    405


<210> SEQ ID NO 25
<211> LENGTH: 376
<212> TYPE: DNA
<213> ORGANISM: Homo sapiens

<400> SEQUENCE: 25

tacagaaatg caaaatgctc tggaaaatct gagcaagatt tcaggtccag gaagactggt     60

gagcaggtgt cagagagact tggtgggttg tcatcaagta ggactaccct tgaacctgtg    120

caaaagagac actaacttgg tgagctcctt ctcaaaggaa catatagggc cacagctggc    180

tcttactcat aagcaccatc tactggtctt taggccagac tgcacagccc aatataaaac    240

ctgcctagga aagtgcatag cctaagaccc tatccagcat attctacagt cacacaccct    300

aggaagggga ggaaatgtca agaaaaaaat atataaagaa acaaacaaaa aatcctatct    360

gcatgaaaat aattac                                                    376


<210> SEQ ID NO 26
<211> LENGTH: 322
<212> TYPE: DNA
<213> ORGANISM: Homo sapiens

<400> SEQUENCE: 26

gagtacgcct gcgcgtgccg ccatttcctg cagccgcaga ctctgcctgc ggtgctcgcc     60

gggaaatgag acgatcaaca aagaaaatgg ttgttttggg cgagatcgac cgtggagagg    120

ctttttctgc agcagtcccg gttcctgccg ccagatggcg ctcgaggatc acaaatgggt    180

ctagggttct cataatggcc ccgcctaaga aattttggat tctcctggcc cttccccccct    240

ttgtggggtc aacagcggat ttgggaatct ggtgaccaac acgtgcgcac tcccctaccc    300

ttgcccctac cgagccctcc ag                                             322


<210> SEQ ID NO 27
<211> LENGTH: 627
<212> TYPE: DNA
<213> ORGANISM: Homo sapiens

<400> SEQUENCE: 27

cttatctttt gattttttga tagtagccac tctgactgga gtgaggtgat gtctcactgc     60
```

```
agttttgatt tgcatttccc tgatgagtga tgttgggcac ctgttcatat agcacccggt    120

gccttatttt gtacatttgg tgaggtcttg gttccctgaa tattattatt gatacttgtg    180

ggcatgtgac aagtctgtgt gtcgaaagac taggtattta ttccagtctt caaagactga    240

cgttgtcccc gtccttccag agcctctaag ccttctgtta ccgtctctga acctctttca    300

ctgctgctgt ttcagcacta gatggcaccc taagcccacg tttgccacaa gtccgtggtt    360

tgtgtgttgc cacattttca gcactagagg gcgcgctgag cccaggtgtg cctgtgacct    420

tgtttccgag ggacctaaaa agcttcggtg agtttccgcc ttaggctggg gcaggtccag    480

atgctccatt ccggcgctgc agagttctgc ctagctctgg gcttcacttt ggtgggtcca    540

gcactgggct ccaaggcaac gtcttgaggc tacttctctc tcctttccct aagcagacgc    600

tgcctctctt tgtgcccggc ggcctgg                                        627


<210> SEQ ID NO 28
<211> LENGTH: 488
<212> TYPE: DNA
<213> ORGANISM: Homo sapiens

<400> SEQUENCE: 28

tgaattagcc ggtcgggtgg cccccagcct tatagcttcg aattctgtga tcctatttta     60

gacccagact tgtccgcgaa gggaaatgaa gaggcgcgga aggcttggag cgtgaaccaa    120

aaaacaatgg gtggggatcg tctaaccagc tcccttccct agaagggcgg aaacggcttt    180

cgaagcatcc gcgattctct ttattgaatc ttgagtgaca cctagtggcc catccgcctc    240

accgtcacgg cgatgctggt ttcactgggc ttttcagaag gcgtgctggc ctgcccatgg    300

ttctcggcta aaagactttg gagcgtaggg tgccgatgaa gtttcctggg accttccgga    360

agcacttgct gtcccgtcaa cagccctgta cctgcgatgc atgcaattct aatgaaaatg    420

cccttctcgt ctggagggct tgcttgagca catcctgagc tctcaggcag caaatataga    480

gtcgggtg                                                             488


<210> SEQ ID NO 29
<211> LENGTH: 416
<212> TYPE: DNA
<213> ORGANISM: Homo sapiens

<400> SEQUENCE: 29

gagcctctgc tctggggctg ccggtcgggc cgtgtgtgct gtgtctcttt aaggaccagg     60

cctcttcaag gcaagttccc tctgcagtcc agtcctgcct ctgcccgtcc tgcggcagag    120

agtgggggct ccccagcgcc atctggcggc cgcacagcag cacctcggcc accagaggct    180

tccagccaag cggcccgcaa gtgcctggac aaaaatctcc agcttggaca cagggctgca    240

ggctgctgtt gggaacacag ctgggggagt caggaggagc tccgtctggg aaggagagag    300

cagaagcccc caggagtgac atggggagaa tgatcatccc gccggacaaa accttcacta    360

aaatatcctc aaatgggccg ggtgtggcag ctcacacctg taatcccagc actttg        416


<210> SEQ ID NO 30
<211> LENGTH: 167
<212> TYPE: DNA
<213> ORGANISM: Homo sapiens

<400> SEQUENCE: 30

ctgtaagcaa gagggccctg cagttgtcct agtcgccagt agggggcgca atggcagagc     60

accgtgggca agctggtcct gtagtgcccg gctgcaagca gggggcgccc gaaacgggct    120
```

```
tttcagatta ctcaggttca actcgtctct gcgccgcgcc gccgggg              167


<210> SEQ ID NO 31
<211> LENGTH: 352
<212> TYPE: DNA
<213> ORGANISM: Homo sapiens

<400> SEQUENCE: 31

tcaaagacag aatccaaaaa ggctgctttc ggggaaaagt ggcctgagag tcaggccttg     60

ttggacaagt tcccctaacg tgctaagcag agacctgttt cacaggccaa aagagcatgg    120

aagctcagcc agagggaccc aggcgggccc acctcacgcc tgtgttcctc ggcagcctct    180

gctgcccccct ggtggccatg ctgtgcacac cgccaccaga cgagggcgcc acccacaggc   240

accacctgct cccaccctca ggcagtattt caatggtccc gtggctctgg gccacgccca    300

catgactagc agccacagct gatcccatgg cctgttggcc accccatcag ca            352


<210> SEQ ID NO 32
<211> LENGTH: 340
<212> TYPE: DNA
<213> ORGANISM: Homo sapiens

<400> SEQUENCE: 32

aaactcctag tctttctaac tttaataact gttcatttgc cactgtccca cagtggcttc     60

tgagatgtca gggacttctc agaggagctg gtggcccagg ctcgtgcttt agctgggctc    120

tcctattgag ctttctccag gctccagcga tgctcctttg cattctgctg ctcccttatg    180

gccatgactg taattacagc taagtttaca gccctggaag aggtttccaa gggagggagg    240

caggaatctg aaagaacatt ggagcatcaa ccaagaaaat aaagaatttg caaatgagga    300

aaaaaagaga gaagaaaaaa gagaaaagag gaggaggatg                          340


<210> SEQ ID NO 33
<211> LENGTH: 368
<212> TYPE: DNA
<213> ORGANISM: Homo sapiens

<400> SEQUENCE: 33

tctcaaccag ctcctgtgaa tgtggccttt tgggcacctt ccttatttcc ccagcagcct     60

ttcccagaca tggattttga tttctcgtct ttctttgtct acagccccag cataaatgcc    120

tgctctcaag cctcaatgtg gcatccaaga catgagccca ggatggtgcc tcaggttcac    180

caaggagtga agtccagcag gtagaggtta ctttacacaa ttccccagga ggccaccaga    240

tggcattgtc agatcatttt acacctactt actgggaagg ggggtgtttc aatagggtag    300

gtggttgaag taacaggtat tatgttggaa aaattatgac aaaaaaggtt gtattttatt    360

tgtggagc                                                             368


<210> SEQ ID NO 34
<211> LENGTH: 509
<212> TYPE: DNA
<213> ORGANISM: Homo sapiens

<400> SEQUENCE: 34

actccagcct gggtgacaca gcgagactcc atgccgtgac accagcacgt ggcgtgtcac     60

attattaagg attatacagc caacagttac tgggctggtt tcctttaatc ctcacagcag    120

gccctgtccg caagtctttc accgtttccc gtcaacactc cacctttcct gcccaaagtt    180
```

```
tggggttggg agggaattcc caggggttcc caggacttgg gctcgcctcc cagatcccgc    240

aacctttgcg tgcctagcct cggcaatgac cgcccatctg ccacgagggg gcggcagcgc    300

accgttcaga cgctgcgccc ctggtgcatt atgggtcgcg tagtctcaaa ggtggcataa    360

gcatcctgga acgcaaacgg catttcccag aaaactacgc gacaatctga gcctggtctt    420

gcccagagct ggaagctgag gtctcgcccc tgccggcgtt gcgggggatt gtgggatgta    480

ggcatttggc tccgcgctcc gcgaagggc                                      509


<210> SEQ ID NO 35
<211> LENGTH: 649
<212> TYPE: DNA
<213> ORGANISM: Homo sapiens

<400> SEQUENCE: 35

cgggtggaac ctgagtaatc tgaaaagccc ggttcgggtg ccccctgctt gtacccgggc     60

actacaggac ccgcttgccc acggtgctgt gccattgcgc cccctgctgg cgactagggc    120

aactgcaggg ccctcttcct tacagtggtg tccagcgccc cctgccggtg ccggggcacg    180

gcagggctct cttgctcgca gtatactggc ggcacgccgc ctgctggcag ctagggacat    240

tgcagggccc tcttgctcac attgtagtgg cagcacaccc gcctgctggc agctggggac    300

actgctgggc cctcttgctt gcagtgtagt cggggcatgc cctcttctgt ccgctggggg    360

cactacagga tcctcttgct cacagtgtag tggcagcacg ccccctgctg gcaaccaggg    420

cacttcacgg tcctcttgct catggtgtgg tgcccctacg ccacctcctg gcagctaagg    480

acactgcagg gccctcttgc tcacagtgta gtcgtcgttc gccccctgct ggcagctagg    540

gacactgccg ggccctcttg ctgacactgt cgtggctgca cgccacctgc aggcagatgg    600

ggactaggca gggccctctt gctcccggtg tgacggctgg cgtcccccta                649


<210> SEQ ID NO 36
<211> LENGTH: 379
<212> TYPE: DNA
<213> ORGANISM: Homo sapiens

<400> SEQUENCE: 36

attcggcatt gacgggtctc tggttcttca agttttcatc tgaaagtctc agtctttgct     60

atcacaacca acgccccctt cctacactcc aaggttgatg gaatgaaatg tcttggaatt    120

gagggtttaa ttaattcgga tcactggaga gaaagaaaag aaataacggg ggaaaaaaat    180

gtgttaattt tagggcttgg aattggaaac gtggggaaac gtcgccacct tctggtaagt    240

gatggaaatg agcaggaaaa aagatccaag ctaagaagcg gctttttttt ttttccaaag    300

cagcaagcca cgcccctccc gcgctcgcga aatccgagac ccgccctttc cggaagtttt    360

gacactgtgc gccccgagt                                                 379


<210> SEQ ID NO 37
<211> LENGTH: 564
<212> TYPE: DNA
<213> ORGANISM: Homo sapiens

<400> SEQUENCE: 37

agatagaggt atatacactt actcagacat atatatataa attctgaggt tcactgacca     60

taaaaagtcc taccatggtt gccaggttaa gaaccctgaa tgtaaggaaa gaaacgaaat    120

taatgtggtt aaagagctga aagctctttg ggtagccgtc aagaatacgt ggagaagaat    180

aggaacgcca gacccagggg ggtccaaggc tggcgtccct agtgccacag tgccctctgg    240
```

tggtagatca taatcattgc tgcgtactcc caggccagag gaagaaatgt aggactcgga 300
aaatgccgga gtccactctg tctcccctca agcctccaga tttgtacacc catctgtcct 360
tcagtcatct tccccacagc ccatctctta ggaatttgat atctcttaag gcagtgaaat 420
gtttctcaga gtgaggccca aggacagttt actcaacagg tcctcaggta gacagatagt 480
ttcagaggac aaagtgatca acaattttgt tcctctactt ttcacagatc tgaaaaatga 540
cagcgattat ggctgtgaca gaaa 564

<210> SEQ ID NO 38
<211> LENGTH: 592
<212> TYPE: DNA
<213> ORGANISM: Homo sapiens

<400> SEQUENCE: 38
gatatctgac agtgccttgt accccagata gacgtgtgtt tatcaagtca cacagtgact 60
tggagaccgc catagtttta ccctgaccaa gactgtcata gagcttggct tctaacctca 120
gcagaaggct tgctcatgtc catgcactta gtcggtttat tctagtttca cgaagtggag 180
gtttttgatt tctaatctgg cacagatgct ccatcccgtg ccttctccag ggatgttttc 240
tgagatcacc caggttttac caggttttat ggggcgagaa cctgtcctca cttaaaaagt 300
aaggaagtta tgccccctgc aggacaaatc ggtaactgca ggctcggtga tctgcgagga 360
cagtgttctg tgccttttgg agcactatat tgtttctctc cacaatgtgg cgctgctgtt 420
ctaagtgtca ttttagggcc agtttagggt aggaaagagg gtgacagcaa gaattagaag 480
gtgtagggga gggcgccagg gaagtaggga aaggagatgt taggaagaaa gctggtgggc 540
tacttctgcc agatagggct tccctagcac cccaaatctg atccattgca at 592

<210> SEQ ID NO 39
<211> LENGTH: 381
<212> TYPE: DNA
<213> ORGANISM: Homo sapiens

<400> SEQUENCE: 39
agaccagcgc ttctggggga ctccttgcca ttagaacctt cctggggctg attcatggcc 60
aggcctggtc ccccagggga gaacagaacc gacaagtctg aggagcacct atagaccgtg 120
gtcctcccca gcctttagca gggagcccac cagcctgcca gccgccctct ggcgccccgc 180
cgggcctggc ctctacctgc ctctgccccc agcgcccaga aggtggcggc atcgctccac 240
ccacaggagc ccttgccgta cccaagtggg aggttcggct tccttcaccc ctcacttccc 300
actgcatggt tttcctggga gggtgtggtg ggttggggtg gggtgggctg gggcgtgggg 360
agagcagact tccgatgtct a 381

<210> SEQ ID NO 40
<211> LENGTH: 571
<212> TYPE: DNA
<213> ORGANISM: Homo sapiens

<400> SEQUENCE: 40
ctccaccagg agccagggaa caggacccgg gcaggtacag cggtaccacc tgttccttac 60
catgcaaatt tattggtaaa aatgaacttt tttcattgtt cagtttttca aacgataatt 120
tcacttcatc cttctggcat attatgctag tagcaataac tggctagtcc ctacacctgc 180
cttggcggca gcgcatctca cttgtgtgaa aggcctgcac acttcaggtg gatgtagaac 240

-continued

```
aagccctccc gctggaggcg cgatcattca ctgcccccta gtggaccaga tgtgcatgag    300

ccaggatccg tgcttccgct ttgatgtggg ctctgagcaa atcagagctg cattttattt    360

cagtaagttt tcggcctctg ctgctttaat ctttgttgct agtgtctacg gttcttaatt    420

aacagccctg aaatggaata aaatgtcaat caagggtgac tctgtgtaaa gctatattta    480

aatgttaaaa agtcgtgaca ttttcaaaca gtatttcagg cctcatttga tgctcatttt    540

aaaaatcaaa ttttcattag gttataaaaa t                                   571
```

GENOMIC INSULATOR ELEMENT EXHIBITING ENHANCER BLOCKING ACTIVITIES IN LYMPHOCYTES AND USES THEREOF

INTRODUCTION

This patent application is a U.S. National Stage application of PCT/US2021/031210, filed May 7, 2021, which claims the benefit of priority from U.S. Provisional Serial No. 63/024,651, filed May 14, 2020, the contents of which are incorporated herein by reference in their entirety.

This invention was made with government support under grant nos. HL053749 and HL111804 awarded by the National Institutes of Health. The government has certain rights in this invention.

BACKGROUND

Hematopoietic stem cell gene therapy has significantly impacted the treatment of several inherited diseases including X-linked SCID, adenosine deaminase deficiency, X-linked adeno-leukodystrophy and beta thalassemia. However, genotoxic side effects, secondary to vector-mediated insertional mutagenesis, occur in a proportion of patients, including T-cell leukemia due to oncogene activation. While the 400 bp fragment of chicken β-globin HS4 insulator (cHS4) has been incorporated into a number of vectors in an attempt to reduce enhancer-mediated oncogenic activity, it has been shown that cHS4 does not effectively block enhancer-mediated effects in T cells, despite its proven activity in myeloid cells (Zhou, et al. (2016) *Mol. Ther.* 24(6):1090-1099; Aker, et al. (2007) *Hum. Gene Ther.* 18:333-343; Arumugam, et al. (2009) *PLoS One.* 4:e6995; Arumugam, et al. (2009) *Mol. Thor.* 2009; 17:1929-1937). While additional insulating polynucleotides have been suggested (WO 2001/092483 A1, WO 2009/016206 A1, WO 2015/138852 A1, US 2003/0211581 A1), there remains a need for improved insulators that decrease the risks of insertional mutagenesis in lymphocytes.

SUMMARY OF THE INVENTION

This invention provides a construct including at least one copy of a genomic insulator element having a core sequence selected from the group of CACTGCCCTCCAGTGGCCA (SEQ ID NO:1), CAGCGCCACCTGCAGGCCA (SEQ ID NO:2), CTTCCAGCAGGAGGAGGCA (SEQ ID NO:3), TGGCCGCTAGAGGGCACGC (SEQ ID NO:4), AAGCACCATCTACTGGTCT (SEQ ID NO:5), CTGCCGCCAGATGGCGCTC (SEQ ID NO:6), TCAGCACTAGATGGCACCC (SEQ ID NO:7), GAGTGACACCTAGTGGCCC (SEQ ID NO:8), CAGCGCCATCTGGCGGCCG (SEQ ID NO:9), TCGCCAGTAGGGGGCGCAA (SEQ ID NO:10), TGCTGCCCCCTGGTGGCCA (SEQ ID NO:11), TGCTGCTCCCTTATGGCCA (SEQ ID NO:12), AGGCCACCAGATGGCATTG (SEQ ID NO:13), CTGCCACGAGGGGGCGGCA (SEQ ID NO:14), TTGCGCCCCCTGCTGGCGA (SEQ ID NO:15), CGTCGCCACCTTCTGGTAA (SEQ ID NO:16), CAGTGCCCTCTGGTGGTAG (SEQ ID NO:17), TTATGCCCCCTGCAGGACA (SEQ ID NO:18), CGCCCAGAAGGTGGCGGCA (SEQ ID NO:19), and CACTGCCCCCTAGTGGACC (SEQ ID NO:20). In some embodiments, the genomic insulator element is 150 bp to 650 bp in length. In particular embodiments, the genomic insulator element has a sequence selected from the group of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39 and SEQ ID NO:40. In certain embodiments, the construct is a a transgene cassette, transposon system or a viral vector e.g., a retroviral vector such as a lentiviral vector. In other embodiments, the construct is a gene therapy vector and may include a sequence encoding a therapeutic agent, e.g., a gene of interest, a protein, a dominant negative mutant, an RNA interference agent, or an miRNA. A host cell (e.g., a lymphocyte), a pharmaceutical composition, and method for treating a disease, e.g., a primary immunodeficiency, haemoglobinopathy or inborn error of metabolism, using the construct are also provided.

DETAILED DESCRIPTION OF THE INVENTION

Human genome-derived DNA fragments of about 150-650 bp in length have now been identified that exhibit strong enhancer blocking activities in T lymphocytes. Such strong insulator activity when used in combination with the administration of an exogenous nucleic acid sequence can, for example, prevent oncogene activation. Thus, this invention provides compositions including constructs encoding at least one copy of a genomic insulator element and uses thereof in the treatment of disease. The compositions and methods described herein have the advantage of reducing tumor formation compared to gene therapy constructs lacking the genomic insulator element(s) of this invention.

Chromatin insulators can decrease the risk of insertional mutagenesis by disrupting the interactions between the enhancers in gene therapy constructs and the regulatory elements of cellular oncogenes. There are two kinds of chromatin insulators: barrier insulators, which protect chromosomal domains from heterochromatinization, and enhancer-blocking insulators, which prevent the interaction between regulatory elements of different chromatin loci. Certain elements combine barrier- and enhancer-blocking activities. The most extensively studied chromatin insulator is located in DNase I hypersensitive site 4 of the Locus Control Region of the chicken beta globin locus (cHS4). Extensive studies have demonstrated that the enhancer-blocking activity of cHS4 insulator depends on binding of the transcriptional factor CTCF. Occupancy by CTCF genome-wide has been surveyed across a large number of cell types and its binding sites are surprisingly conserved across species. A large fraction of CTCF binding sites genome-wide overlap with cohesin proteins, and insulator function at cHS4 is reportedly dependent upon cohesin. Furthermore, CTCF sites are enriched at topological associating domain boundaries.

Several studies have addressed the role of chromatin insulators in gene therapy, mostly by incorporating cHS4 or its components in viral vectors. cHS4 decreases the probability of vector silencing by its barrier function, the probability of activation of proximal regulatory elements by its enhancer-blocking function, and the risk of genotoxicity in ex viva and in viva assays. However, the cHS4 insulator has two disadvantages: the fully active cHS4 element is very large (1.2 kb) and consumes precious space in viral vectors; the incorporation of the full-length cHS4 often results in diminished vector titers, and cHS4 exhibits weak insulator activity in lymphocytes.

As indicated, the construct of this invention includes at least one copy of a genomic insulator element. For the purposes of this invention, the term "genomic insulator element" refers to a nucleic acid sequence that prevents the activation or upregulation of a gene (e.g., a neighboring gene). Such genomic insulator elements can include a barrier function to protect chromosomal domains from heterchromatinization and/or an enhancer-blocking function to prevent the interaction between regulatory elements of different genomic loci.

The genomic insulator elements provided herein include enhancer-blocking to reduce the probability of activation of proximal regulatory elements. However, the genomic insulator elements described herein are shorter than the active cHS4 element, can be easily incorporated into nucleic acid constructs, and exhibit strong enhancer blocking activities in lymphocytes.

In one embodiment, the genomic insulator elements described herein are less than 650 bp in length. In other embodiments, the genomic insulator elements are less than 600 pb, less than 550 bp, less than 500 bp, less than 450 bp, less than 400 bp, less than 350 bp, less than 325 bp, less than 300 bp, less than 290 bp, less than 280 bp, less than 270 bp, less than 260 bp, less than 250 bp, less than 240 bp, less than 230 bp, less than 220 bp, less than 210 bp, less than 200 bp, less than 190 bp, less than 180 bp, less than 170 bp, or smaller.

In other embodiments, the genomic insulator elements described herein are between 150-650 bp in length, between 200-600 bp, between 300-600 bp, between 400-600 bp, between 500-600 bp, between 125-300 bp, between 150-300 bp, between 175-300 bp, between 200-300 bp, between 225-300 bp, between 250-300 bp, between 275-300 bp, and any range therebetween.

It has been found that a 19 bp core sequence in each of the genomic insulator elements is essential for insulator activity. The core sequences of the genomic insulator elements of this invention are provided in Table 1.

TABLE 1

| Insulator | Sequence | SEQ ID NO: |
|---|---|---|
| C01 | CACTGCCCTCCAGTGGCCA | 1 |
| C02 | CAGCGCCACCTGCAGGCCA | 2 |
| C03 | CTTCCAGCAGGAGGAGGCA | 3 |
| C04 | TGGCCGCTAGAGGGCACGC | 4 |
| C05 | AAGCACCATCTACTGGTCT | 5 |
| C06 | CTGCCGCCAGATGGCGCTC | 6 |
| C07 | TCAGCACTAGATGGCACCC | 7 |
| C08 | GAGTGACACCTAGTGGCCC | 8 |
| C09 | CAGCGCCATCTGGCGGCCG | 9 |
| C010 | TCGCCAGTAGGGGGCGCAA | 10 |
| C011 | TGCTGCCCCCTGGTGGCCA | 11 |
| C012 | TGCTGCTCCCTTATGGCCA | 12 |
| C013 | AGGCCACCAGATGGCATTG | 13 |
| C014 | CTGCCACGAGGGGGCGGCA | 14 |
| C015 | TTGCGCCCCCTGCTGGCGA | 15 |

TABLE 1-continued

| Insulator | Sequence | SEQ ID NO: |
|---|---|---|
| C016 | CGTCGCCACCTTCTGGTAA | 16 |
| C017 | CAGTGCCCTCTGGTGGTAG | 17 |
| C018 | TTATGCCCCCTGCAGGACA | 18 |
| C019 | CGCCCAGAAGGTGGCGGCA | 19 |
| C020 | CACTGCCCCCTAGTGGACC | 20 |

While the core sequences of the genomic insulator elements are essential for activity, in certain aspects, the core sequences are in the context of the genomic insulator element sequences provided in Table 2 to provide optimal insulator activity.

TABLE 2

| Insulator | Coordinate[1] | Sequence[2] | SEQ ID NO: |
|---|---|---|---|
| C01 | chr14: 69283376-69283839 | GCGAGGGGAGACACAGGGGCCGGGGCTGCG GCGGCTGAGCTCCCTGGGCGGCTCGGAACG CAAGGGGCCGGCGAGCCGACGCTGCTGCAG GAGGCTGCGGCGTGGGGCGAGGTTCTCGCT ACGGCTTCGTTCCCGTCCTCCCGCGGCCGC TCTCCCCCGGAAGCCCTCGGAGGCAGCACG ATGGACGTGGCCACACTGCCCTCCAGTGGC CAGCTCGCCGAACAACACGTCTGGGCCCCT TTTGGGGGTCTGGGTGACGTGTCCACCCTC TCTCTGCCCTTTGCTACATTTGAAGGTGGG GTTTGCTCATCCATGGTTCCTCTTACAGGT CACCAAAGCTGCCACAGTGCACACTCACCC AACAGCAGGGGATTTGCCGCCTTcggtggt tctcaaacttcagtgtgcacaggaatcccc ccttggacagttctttcaaacccggattgc tgggtcccccaac | 21 |
| C02 | chr17: 16593182-16593576 | CTGACCCGTACCCCTGAACCGAGCAAGCCT AGGAGCAGGTGCGCCGGCGGCGCTGTGAAG CGGCACTCATGACAGGCAGGCTGGGCACCG CCACCCCGAAACCTCCGAGGGAGGACCAGC CAGCCCAGGTTGGCGCTGGAGCTGCAGCGC CACCTGCAGGCCAAGGAGTCTTTTTCTGGG AGGCTGGAGCTGCAGCGCCACCTGCAGGCC AAGGAGTCTTTTTCTGGGAGGCTGGAGCTG CAGCGCCACCTGCAGGCCAAGGAGTCTTTT TCTGGGAGGCTGGAGCTGCAGATGCAGTGA AGTCACAGGTTCCGTGATGTCACAGGTGGG CAGGCGCACTGGTCTGTAACGGATTGGCTT GGCCTTACCCACGAGGCTTTGCGGTGGCTG TTGG | 22 |
| C03 | chr10: 82265148-82265737 | GTGCTGGGGAGGCAGTGAGGGCTGAAAAAG GCCAGGGAGGGAAGAGGGGAGGGGAGGGAA GCAGTAAGGTGGAGCAGGCCTGGCCAGAAA GAGCCAGGAATAAAGCTTCCTCTAGTGTCT TGAGCCTAGGCCTTCTTCCTTCAGTGGAAC CTCCCTTTGCTTCCAGCAGGAGGAGGCAGG AGAACCTAGGTCTACAGGCTTTCCTGCCAT GGTCTTAGGGACTGGATAAGGCCCACCTTC AGGTTTGGGCACCTTCCAAGTGGCCTGTGA ACCCCTAAAGGGCAAGAGCTGGGGTACGAT GTCCCTTTGCCCCAGTGACCCAGAAGCAGG TTCAATCTGTGCCTCACAGCACCACCGTGT GGCTTCCCCTGGGACTGCAGCCGCCTAACT GGGTGTGGCCCTGAGTGTGGAGCTGGCTAC TACAATTCCTTTGAATctgtcgatctaaaa taagtgaaaaggccagaacctagtttagag agagtttattcaagcacacatgttgaggac aggcctacccaggaagcacaaattccaaag aatggaagtcagccttcctgttcgaaatgt aggagcttgggatcattta | 23 |

TABLE 2-continued

| Insulator | Coordinate[1] | Sequence[2] | SEQ ID NO: |
|---|---|---|---|
| C04 | chr2: 96658540-96658945 | TCCCAAGGCTGCTGCCTGCATGCCACTCCGtgaggaagttgaaatacatggtctctaagattccttccagctctTCACCTCATGAGACATATAAATCAAGTAACATTCGTTATTGTGATTAGAAAAGCTGCATTTACACACGTTAGCCACTAGATGGGGACGTGCGATTGTTACAATGCTGAAGGTTTCCCGTATTTCTTTATTTTTTATTTGGCCGCTAGAGGGCACGCCTGCACTGCACTTAAAGTTGACTACTTTCAAGGAAAGACAAAGGAATTCTTGGATTTCTCCATTTTCCTCATCACCTGTGCTTATCAGAGAATTCCAGGGGCAAGCTACCCTTTCCAATTCATCACTAACTTATAAACAAAATTCTAAGGAGTAAGGAATGCTTCTTACTTACTT | 24 |
| C05 | chr11: 58053732-58054108 | tacagaaatgcaaaatgctctggaaaatctgagcaaGATTTCAGGTCCAGGAAGACTGGTGAGCAGGTGTCAGAGAGACTTGGTGGGTTGTCATCAAGTAGGACTACCCTTGAACCTGTGCAAAAGAGACACTAACTTGGTGAGCTCCTTCTCAAAGGAACATATAGggccacagctggctcttactcataagcaccatctactggtctttaggccagactgcacagcccaatataaaacctgcctaggaaagtgcatagcctaagaccctatccagcatattctacagtcacacaccctaggaaggggaggaaatgtcaagaaaaaaatatataaagaaacaaacaaaaaatcctatctgcatgaaaataattac | 25 |
| C06 | chrX: 152127459-152127781 | GAGTACGCCTGCGCGTGCCGCCATTTCCTGCAGCCGCAGACTCTGCCTGCGGTGCTCGCCGGGAAATGAGACGATCAACAAAGAAAATGGTTGTTTTGGGCGAGATCGACCGTGGAGAGGCTTTTTCTGCAGCAGTCCCGGTTCCTGCCGCCAGATGGCGCTCGAGGATCACAAATGGGTCTAGGGTTCTCATAATGGCCCCGCCTAAGAAATTTTGGATTCTCCTGGCCCTTCCCCCCTTTGTGGGGTCAACAGCGGATTTGGGAATCTGGTGACCAACACGTGCGCACTCCCCTACCCTTGCCCCTACCGAGCCCTCCAG | 26 |
| C07 | chr10: 65800779-65801406 | cttatcttttgatttttgatagtagccactctgactggagtgaggtgatgtctcactgcagttttgatttgcatttccctgatgagtgatgttgggcacctgttcatataGCAcccggtgccttattttgtacatttggtgaggtcttggttccctgaatattattattgatacttgtgggcatgtgacaagtctgtgtgtcgaaagactaggtatttattccagtcttcaaagactgacgttgtccccgtccttccagagcctctaagccttctgttaccgtctctgaacctctttcactgctgctgtttcagcactagatggcaccctaagcccaCGTTTGCCACAAGTCCGTGGTTTGTGTgttgccacattttcagcactagagggcgcgctgagcccaggtgtgcctGTGACCTTGTTTCCGAGGGACCTAAAAAGCTTCggtgagtttccgccttaggctggggcaggtccagatgctccattccggcgctgcagagttctgcctagctctgggcttcactttggtgggtccagcactgggctccaaggcaacgtcttgaggctacttctctctcctttccctaagcagacgctgcctctctttgtgcccggcggcctgg | 27 |
| C08 | chr12: 94495978-94496466 | TGAATTAGCCGGTCGGGTGGCCCCCAGCCTTATAGCTTCGAATTCTGTGATCCTATTTTAGACCCAGACTTGTCCGCGAAGGGAAATGAAGAGGCGCGGAAGGCTTGGAGCGTGAACCAAAAAACAATGGGTGGGGATCGTCTAACCAGCTCCCTTCCCTAGAAGGGCGGAAACGGCTTTCGAAGCATCCGCGATTCTCTTTATTGAATCTTGAGTGACACCTAGTGGCCCATCCGCCTCTTTTCAGAAGGCGTGCTGGCCTGCCCATGGTTCTCGGCTAAAAGACTTTGGAGCGTAGGGTGCCGATGAAGTTTCCTGGGACCTTCCGGAAGCACTTGCTGTCCCGTCAACAGCCCTGTACCTGCGATGCATGCAATTCTAATGAAAATGCCCTTCTCGTCTGGAGGGCTTGCTTGAGCACATCCTGAGCTCTCAGGCAGCAAATATAGAgtcgggtg | 28 |
| C09 | chr17: 1090526-1090942 | GAGCCTCTGCTCTGGGGCTGCCGGTCGGGCCGTGTGTGCTGTGTCTCTTTAAGGACCAGGCCTCTTCAAGGCAAGTTCCCTCTGCAGTCCAGTCCTGCCTCTGCCCGTCCTGCGGCAGAGAGTGGGGGCTCCCCAGCGCCATCTGGCGGCCGCACAGCAGCACCTCGGCCACCAGAGGCTTCCAGCCAAGCGGCCCGCAAGTGCCTGGACAAAAATCTCCAGCTTGGACACAGGGCTGCAGGCTGCTGTTGGGAACACAGCTGGGGGAGTCAGGAGGAGCTCCGTCTGGGAAGGAGAGAGCAGAAGCCCCCAGGAGTGACATGGGGAGAATGATCATCCCGCCGGACAAAACCTTCACTAAAATATCCTCAAATGggccgggtgtggcagctcacacctgtaatcccagcactttg | 29 |
| C010 | chr19: 59117900-59118067 | ctgtaagcaagagggccctgcagttgtcctagtcgccagtagggggcgcaatggcagagcaccgtgggcaagctggtcctgtagtgcccggctgcaagcagggggcgcccgaaacgggcttttcagattactcaggttcaactcgtctctgcgccgcgccgccgggg | 30 |
| C011 | chr16: 146877-147229 | tcaaagacagaatccaaaaaggctgctttcggggaaaagtggcctgagagtcaggccttgttggacaagtTCCCCTAACGTGCTAAGCAGAGACCTGTTTCACAGGCCAAAAGAGCATGGAAGCTCAGCCAGAGGGACCCAGGCGGGCCCACCTCACGCCTGTGTTCCTCGGCAGCCTCTGCTGCCCCCTGGTGGCCATGCTGTGCACACCGCCACCAGACGAGGGCGCCACCCACAGGCACCACCTGCTCCCACCCTCAGGCAGTATTTCAATGGTCCCGTGGCTCTGGGCCACGCCCACATGACTAGCAGCCACAGCTGATCCCATGGCCTGTTGGCCACCCCATCAGCA | 31 |
| C012 | chr11: 29181140-29181480 | aaactcctagtctttctaactttaataactgttcatttgccactgtcccacagtggcttctgAGATGTCAGGGACTTCTCAGAGGAGCTGGTGGCCCAGGCTCGTGCTTTAGCTGGGCTCTCCTATTGAGCTTTCTCCAGGCTCCAGCGATGCTCCTTTGCATTCTGCTGCTCCCTTATGGCCATGACTGTAATTACAGCTAAGTTTACAGCCCTGGAAGAGGTTTCCAAGGGAGGGAGGCAGGAATCTGAAAGAACATTGGAGCATCAACCaagaaaataaagaatttgcaaatgaggaaaaaaagagagaagaaaaaagagaaaagaggaggaggatg | 32 |
| C013 | chr10: 92511113-92511481 | TCTCAACCAGCTCCTGTGAATGTGGCCTTTTGGGCACCTTCCTTATTTCCCCAGCAGCCTTTCCCAGACATGGATTTTGATTTCTCGTCTTTCTTTGTCTACAGCCCCAGCATAAATGCCTGCTCTCAAGCCTCAATGTGGCATCCAAGACATGAGCCCAGGATGGTGCCTCAGGTTCACCAAGGAGTGAAGTCCAGCAGGTAGAGGTTACTTTACACAATTCCCCAGGAGGCCACCAGATGGCATTGTCAGATCATTTTACACCTACTTACTGGGAAGGGGGGTGTTTCAATAGGGTAGGTGGTTGAAGTAACAGGTATTATGTTGGAAAAATTATGACAAAAAAGGTTGTATTTTATTTGTGGAGC | 33 |
| C014 | chr19: 36618504-36619013 | actccagcctgggtgacacagcgagactcCATGCCGTGACACCAGCACGTGGCGTGTCACATTATTAAGGATTATACAGCCAACAGTTACTGGGCTGGTTTCCTTTAATCCTCACAGCAGGCCCTGTCCGCAAGTCTTTCACCGTTTCCCGTCAACACTCCACCTTTCCTGCCCAAAGTTTGGGGTTGGGAGGGAATTCCCAGGGGTTCCCAGGACTTGGGCTCGCCTCCCAGATCCCGCAACCTTTGCGTGCCTAGCCTCGGCAATGAC | 34 |

TABLE 2-continued

| Insulator | Coordinate[1] | Sequence[2] | SEQ ID NO: |
|---|---|---|---|
| | | CGCCCATCTGCCACGAGGGGGCGGCAGCGC<br>ACCGTTCAGACGCTGCGCCCCTGGTGCATT<br>ATGGGTCGCGTAGTCTCAAAGGTGGCATAA<br>GCATCCTGGAACGCAAACGGCATTTCCCAG<br>AAAACTACGCGACAATCTGAGCCTGGTCTT<br>GCCCAGAGCTGGAAGCTGAGGTCTCGCCCC<br>TGCCGGCGTTGCGGGGGATTGTGGGATGTA<br>GGCATTTGGCTCCGCGCTCCGCGAAGGGC | |
| C015 | chr19:<br>246805-<br>247454 | cgggtggaacctgagtaatctgaaaagccc<br>ggttcgggtgccccctgcttgtacccgggc<br>actacaggacccgcttgcccacggtgctgt<br>gccattgcgccccctgctggcgactagggc<br>aactgcagggccctcttccttacagtggtg<br>tccagcgcccctgccggtgccggggcacg<br>gcagggctctcttgctcgcagtatactggc<br>ggcacgccgcctgctggcagctagggacat<br>tgcagggccctcttgctcacattgtagtgg<br>cagcacacccgcctgctggcagctggggac<br>actgctgggccctcttgcttgcagtgtagt<br>cggggcatgccctcttctgtccgctggggg<br>cactacaggatcctcttgctcacagtgtag<br>tggcagcacgcccctgctggcaaccaggg<br>cacttcacggtcctcttgctcatggtgtgg<br>tgcccctacgccacctcctggcagctaagg<br>acactgcagggccctcttgctcacagtgta<br>gtcgtcgttcgccccctgctggcagctagg<br>gacactgccgggccctcttgctgacactgt<br>cgtggctgcacgccacctgcaggcagatgg<br>ggactaggcagggccctcttgctcccggtg<br>tgacggctggcgtcccccta | 35 |
| C016 | chr12:3<br>8710082-<br>38710461 | ATTCGGCATTGACGGGTCTCTGGTTCTTCA<br>AGTTTTCATCTGAAAGTCTCAGTCTTTGCT<br>ATCACAACCAACGCCCCCTTCCTACACTCC<br>AAGGTTGATGGAATGAAATGTCTTGGAATT<br>GAGGGTTTAATTAATTCGGATCACTGGAGA<br>GAAAGAAAAGAAATAACGGGGGAAAAAAAT<br>GTGTTAATTTTAGGGCTTGGAATTGGAAAC<br>GTGGGGAAACGTCGCCACCTTCTGGTAAGT<br>GATGGAAATGAGCAGGAAAAAAAGATCCAAG<br>CTAAGAAGCGGCTTTTTTTTTTTTCCAAAG<br>CAGCAAGCCACGCCCCTCCCGCGCTCGCGA<br>AATCCGAGACCCGCCCTTTCCGGAAGTTTT<br>GACACTGTGCGCCCCGAGT | 36 |
| C017 | chr12:<br>6394121-<br>6394685 | agatagaggtatatacacttactcagacat<br>atatatataaattctgaggttcactgacca<br>taaaaagtcctaccatggttgccaggttaa<br>gaacccTGAATGTAAGGAAAGAAACGAAAT<br>TAATGTGGTTAAAGAGCTGAAAGCTCTTTG<br>GGTAGCCGTCAAGAATACGTGGAGAAGAAT<br>AGGAACGCCAGACCCAGGGGGGTCCAAGGC<br>TGGCGTCCCTAGTGCCACAGTGCCCTCTGG<br>TGGTAGATCATAATCATTGCTGCGTACTCC<br>CAGGCCAGAGGAAGAAATGTAGGACTCGGA<br>AAATGCCGGAGTCCACTCTGTCTCCCCTCA<br>AGCCTCCAGATTTGTACACCCATCTGTCCT<br>TCAGTCATCTTCCCCACAGCCCATCTCTTA<br>GGAATTTGATATCTCTTAAGGCAGTGAaat<br>gtttctcagagtgaggcccaaggacagttt<br>actcaacaggtcctcaggtagacagatagt<br>ttcagaggacaaagtgatcaacaattttgt<br>tcctctacttttcacagatctgaaaaatga<br>cagcgattatggctgtgacagaaa | 37 |
| C018 | chr10:<br>102193363-<br>102193955 | GATATCTGACAGTGCCTTGTACCCCAGATA<br>GACGTGTGTTTATCAAGTCACACAGTGACT<br>TGGAGACCGCCATAGTTTTACCCTGACCAA<br>GACTGTCATAGAGCTTGGCTTCTAACCTCA<br>GCAGAAGGCTTGCTCATGTCCATGCACTTA<br>GTCGGTTTATTCTAGTTTCACGAAGTGGAG<br>GTTTTTGATTTCTAATCTGGCACAGATGCT<br>CCATCCCGTGCCTTCTCCAGGGATGTTTTC<br>TGAGATCACCCAGGTTTTACCAGGTTTTAT<br>GGGGCGAGAACCTGTCCTCACTTAAAAAGT<br>AAGGAAGTTATGCCCCCTGCAGGACAAATC<br>GGTAACTGCAGGCTCGGTGATCTGCGAGGA<br>CAGTGTTCTGTGCCTTTTGGAGCACTATAT<br>TGTTTCTCTCCACAATGTGGCGCTGCTGTT<br>CTAAGTGTCATTTTAGGGCCAGTTTAGGGT<br>AGGAAAGAGGGTGACAGCAAGAATTAGAAG<br>GTGTAGGGGAGGGCGCCAGGGAAGTAGGGA<br>AAGGAGATGTTAGGAAGAAAGCTGGTGGGC<br>TACTTCTGCCAGATAGGGCTTCCCTAGCAC<br>CCCAAATCTGATCCATTGCAAT | 38 |
| C019 | chr6:<br>37451925-<br>37452306 | AGACCAGCGCTTCTGGGGGACTCCTTGCCA<br>TTAGAACCTTCCTGGGGCTGATTCATGGCC<br>AGGCCTGGTCCCCCAGGGGAGAACAGAACC<br>GACAAGTCTGAGGAGCACCTATAGACCGTG<br>GTCCTCCCCAGCCTTTAGCAGGGAGCCCAC<br>CAGCCTGCCAGCCGCCCTCTGGCGCCCCGC<br>CGGGCCTGGCCTCTACCTGCCTCTGCCCCC<br>AGCGCCCAGAAGGTGGCGGCATCGCTCCAC<br>CCACAGGAGCCCTTGCCGTACCCAAGTGGG<br>AGGTTCGGCTTCCTTCACCCCTCACTTCCC<br>ACTGCATGGTTTTCCTGGGAgggtgtggtg<br>ggttggggtggggtgggctggggCGTGGGG<br>AGAGCAGACTTCCGATGTCTA | 39 |
| C020 | chr13:<br>31618434-<br>31619005 | CTCCACCAGGAGCCAGGGAACAGGACCCGG<br>GCAGGTACAGCGGTACCACCTGTTCCTTAC<br>CATGCAAATTTATTGGTAAAAATGAACTTT<br>TTTCATTGTTCAGTTTTTCAAACGATAATT<br>TCACTTCATCCTTCTGGCATATTATGCTAG<br>TAGCAATAACTGGCTAGTCCCTACACCTGC<br>CTTGGCGGCAGCGCATCTCACTTGTGTGAA<br>AGGCCTGCACACTTCAGGTGGATGTAGAAC<br>AAGCCCTCCCGCTGGAGGCGCGATCATTCA<br>CTGCCCCCTAGTGGACCAGATGTGCATGAG<br>CCAGGATCCGTGCTTCCGCTTTGATGTGGG<br>CTCTGAGCAAATCAGAGCTGCATTTTATTT<br>CAGTAAGTTTTCGGCCTCTGCTGCTTTAAT<br>CTTTGTTGCTAGTGTCTACGGTTCTTAATT<br>AACAGCCCTGAAATGGAATAAAATGTCAAT<br>CAAGGGTGACTCTGTGTAAAGCTATATTTA<br>AATGTTAAAAAGTCGTGACATTTTCAAACA<br>GTATTTCAGGCCTCATTTGATGCTCATTTT<br>AAAAATCAAATTTTCATTAGGTTATAAAAA<br>T | 40 |

Lower case letters represent Repeat Elements.

[1] The Coordinates denote the location in the human genome (hg19).

[2] Core sequences in the elements are underlined.

Also contemplated herein are variants or homologues of the genomic insulator elements listed in Table 2, provided that the variants or homologues retain at least 75%, at least 80%, at least 85%, at least 90%, at least 95%, at least 98%, at least 99% or even 100% of the enhancer-blocking activity of the genomic insulator elements. In some embodiments, it is also contemplated that a variant or homologue of a genomic insulator element listed in Table 2 will have greater enhancer-blocking activity than the sequences provided in Table 2. For example, a variant and/or homologue can have an activity at least 20% higher than the activity of a genomic insulator element sequence listed in Table 2. In other embodiments, the variant and/or homologue can have an activity at least 50% higher, at least 60% higher, at least 70% higher, at least 80% higher, at least 85% higher, at least 90% higher, at least 95% higher, at least 98% higher, at least 99% higher, at least 1-fold higher, at least 2-fold higher, at least 5-fold higher, at least 10-fold higher, at least 20-fold higher, at least 50-fold higher, at least 75-fold higher, at least 100-fold higher, at least 150-fold higher, at least 200-fold higher, at least 500-fold higher, at least 1000-fold higher activity, or more compared to the activity of a genomic insulator element listed in Table 2.

The genomic insulator elements described herein can be used in the design of a nucleic acid construct, e.g., for effecting gene therapy and/or treating a disease. For the purposes of this invention, a "construct" or "nucleic acid construct" are used interchangeably to refer to a nucleic acid molecule intended to be integrated into a genome, preferably for the treatment of a disease. Nucleic acid constructs of this invention include, but are not limited to, viral vectors, transposon systems, transgene cassettes and the like, which may be delivered into cells using a variety of well-established methods.

At a minimum, the constructs described herein include at least one copy of a genomic insulator element. However, constructs including multiple copies (i.e., 2 or more) of a single genomic insulator element or constructs including multiple different genomic insulator elements are also contemplated herein.

Accordingly, in some embodiments, the construct includes at least 1, at least 2, at least 3, at least 4, at least 5, at least 6, at least 7, at least 8, at least 9, at least 10, or more copies of a single genomic insulator element. In other embodiments, the construct includes at least 2, at least 3, at least 4, at least 5, at least 6, at least 7, at least 8, at least 9 or more different genomic insulator elements. Constructs that include at least two different genomic insulator elements can also include at least 1, at least 2, at least 3, at least 4, at least 5, at least 6, at least 7, at least 8, at least 9, at least 10, or more copies of one or more of the genomic insulator elements. One of skill in the art can readily design constructs to include multiple copies or multiple genomic insulator elements which can balance the enhancer blocking activity of the construct with an overall insert size conducive for construct constraints.

In one aspect, a construct is a viral vector. A "viral vector" refers to a virus-derived nucleic acid vehicle that contains a combination of recombinant DNA sequence components for directing transgene expression. As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

Essentially any viral vector can be used with the compositions and methods described herein, particularly since the use of the genomic insulator elements described herein can mitigate the carcinogenic effect of the viral vector in a subject. Viral vectors are known in the art and include, but not limited to, retroviral vectors (e.g., lentiviral vectors), adenoviral vectors, or adeno-associated viral vectors. In certain aspects, the viral vector is gene therapy vector.

In one embodiment, the viral vector including a genomic insulator element as described herein is a retroviral vector. The term "retroviral vector" refers to a viral vector or plasmid containing structural and functional genetic elements that are primarily derived from a retrovirus. Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

The term "retrovirus" or "retroviral vector", as used herein is meant to include "lentivirus" and "lentiviral vectors," respectively. The term "lentivirus" refers to a group (or genus) of complex retroviruses. Illustrative retroviruses include, but are not limited to, HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV-based vector backbones (i.e., HIV cis-acting sequence elements) are preferred.

Also contemplated for use herein are "hybrid vectors." The term "hybrid" refers to a vector, LTR or other nucleic acid containing both retroviral, (e.g., lentiviral sequences) and non-lentiviral viral sequences. Such viral sequences can include, for example, sequences for reverse transcription, replication, integration and/or packaging sequences, non-structural proteins, and/or polymerase recognition sites.

The use of a genomic insulator element is particularly important in vectors that are incorporated into the genome (e.g., retroviral vectors), however the use of an adenoviral vector, an adeno-associated viral vector (AAV), or components thereof can also include a genomic insulator element. The AAV vector can be selected from the group of serotype 1, 2, 3, 4, 5, 6, 7, 8, 9, and 10 or a chimeric AAV derived therefrom (Wu, et al. (2006) *Mol. Ther.* 14:316-27; Bowles, et al. (2012) *Mol. Ther.* 20:443-455). In general, for transduction in mice, AAV serotype 6 and AAV serotype 9 are particularly suitable, while for gene transfer into a human, AAV serotypes 1, 6, 8 and 9 are preferred.

Recombinant viral vectors can be generated according to standard techniques. Prior to their in vivo application viral vectors may be desalted by gel filtration methods and purified by subsequent filtering. Purification reduces potential deleterious effects in the subject to which the vectors are administered. The administered virus is substantially free of wild-type and replication-competent virus. The purity of the virus can be demonstrated by suitable methods, such as sodium dodecyl sulfate-polyacrylamide gel electrophoresis (SDS-PAGE) followed by silver staining.

As will be appreciated by one of ordinary skill in the art, viral vectors are typically preferred for administration of nucleic acid molecules to a subject (e.g., a human), however the genomic insulator element(s) described herein are contemplated for use with any suitable gene therapy vector or even with plasmid or naked nucleic acid sequences.

The constructs described herein can include any number of sequences known to those of skill in the art, such as promoters (e.g., constitutive or inducible), enhancers, long-terminal repeats (LTRs), multiple cloning sites, restriction sequences, and the like. It will be appreciated by those of ordinary skill in the art that a construct can be designed to include any number of optional sequences, e.g., to enhance expression of a therapeutic agent in a subject. Some non-limiting examples of these sequences include, e.g., "construct components" as described herein.

The constructs described herein can contain zero, one or more of the following construct components: promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, or epitope tags.

Promoters used with the constructs described herein can be constitutive, inducible, or tissue-specific. As used herein, the term "constitutive promoter" refers to a promoter that continually or continuously allows for transcription of an operably linked sequence. Constitutive promoters may be a "ubiquitous promoter" that allows expression in a wide variety of cell and tissue types or a "tissue-specific promoter" that allows expression in a restricted variety of cell and tissue types. Illustrative ubiquitous promoters include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EFla) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin ((3-KIN), the human ROSA 26 locus (Orions, et al. (2007) Nature Biotech. 25:1477-1482), a Ubiquitin C promoter (UBC), a phosphoglycerate kinase-1 (PGK) promoter, a cytomegalovirus enhancer/chicken β-actin (CAG) promoter, and a β-actin promoter.

In one embodiment, it may be desirable to use a tissue-specific promoter to achieve cell-type-specific, lineage-specific, or tissue-specific expression of a desired polynucleotide sequence. Illustrative examples of tissue-specific promoters include, but are not limited to: an B29 promoter (B cell expression), a runt transcription factor (CBFa2) promoter (stem cell specific expression), an CD14 promoter (monocytic cell expression), an CD43 promoter (leukocyte and platelet expression), an CD45 promoter (hematopoietic cell expression), an CD68 promoter (macrophage expression), a CYP450 3A4 promoter (hepatocyte expression), an desmin promoter (muscle expression), an elastase 1 promoter (pancreatic acinar cell expression, an endoglin promoter (endothelial cell expression), a fibroblast specific protein 1 promoter (FSP1) promoter (fibroblast cell expression), a fibronectin promoter (fibroblast cell expression), a fins-related tyrosine kinase 1 (FLTI) promoter (endothelial cell expression), a glial fibrillary acidic protein (GFAP) promoter (astrocyte expression), an insulin promoter (pancreatic beta cell expression), an integrin, alpha 2b (ITGA2B) promoter (megakaryocytes), an intracellular adhesion molecule 2 (ICAM-2) promoter (endothelial cells), an interferon beta (IFN-(3) promoter (hematopoietic cells), a keratin 5 promoter (keratinocyte expression), a myoglobin (MB) promoter (muscle expression), a myogenic differentiation 1 (MYOD1) promoter (muscle expression), a nephrin promoter (podocyte expression), a bone gamma-carboxyglutamate protein 2 (OG-2) promoter (osteoblast expression), an 3-oxoacid CoA transferase 2B (Oxct2B) promoter, (haploid-spermatid expression), a surfactant protein B (SP-B) promoter (lung expression), a synapsin promoter (neuron expression), and a Wiskott-Aldrich syndrome protein (WASP) promoter (hematopoietic cell expression).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue-specific expression. Certain embodiments of the methods and compositions herein provide conditional expression of a polynucleotide of interest, e.g., expression is controlled by subjecting a cell, tissue, organism, etc., to a treatment or condition that causes the polynucleotide to be expressed or that causes an increase or decrease in expression of the polynucleotide encoded by the polynucleotide of interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin, et al. (2003) *Gene* 323:67), the cumate inducible gene switch (WO 2002/088346), tetracycline-dependent regulatory systems, etc.

Conditional expression can also be achieved by using a site-specific DNA recombinase. According to certain embodiments, the vector includes at least one (typically two) site(s) for recombination mediated by a site-specific recombinase. As used herein, the terms "recombinase" or "site-specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see, e.g., bandy (1993) *Curr. Opin. Biotech.* 3:699-707), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The constructs may include one or more recombination sites for any of a wide variety of site-specific recombinases. It is to be understood that the target site for a site-specific recombinase is in addition to any site(s) required for integration of a construct, e.g., a retroviral vector or lentiviral vector. As used herein, the terms "recombination sequence," "recombination site," or "site-specific recombination site" refer to a particular nucleic acid sequence which a recombinase recognizes and binds.

For example, one recombination site for Cre recombinase is loxP, which is a 34-base pair sequence including two 13 base pair inverted repeats (serving as the recombinase binding sites) flanking an 8-base pair core sequence (see, e.g., Sauer (1994) *Curr. Opin. Biotech.* 5:521-527 (1994)). Other exemplary loxP sites include, but are not limited to, lox511, lox5171, lox2272, m2, lox71, and lox66.

Suitable recognition sites for the FLP recombinase include, but are not limited to, FRT, F1, F2, F3, F4, F5, FRT(LE), FRT(RE). Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length).

In one embodiment, the constructs described herein can include an "internal ribosome entry site" or "IRES," which refers to an element that promotes direct internal ribosome entry to the initiation codon, such as ATG, of a cistron (a protein encoding region), thereby leading to the cap-independent translation of the gene. In particular embodiments, the constructs contemplated herein may include one or more genes of interest that encode one or more polypeptides (e.g., therapeutic proteins). To achieve efficient translation of each of the plurality of polypeptides, the polynucleotide sequences can be separated by one or more IRKS sequences or polynucleotide sequences encoding self-cleaving polypeptides.

As used herein, the term "Kozak sequence" refers to a short nucleotide sequence that greatly facilitates the initial binding of mRNA to the small subunit of the ribosome and increases translation. The consensus Kozak sequence is described in Kozak (1986) Cell 44(2):283-92 and Kozak (1987) Nucleic Acids Res. 15(20):8125-48).

In particular embodiments, constructs include a polyadenylation sequence 3' of a polynucleotide encoding a polypeptide to be expressed. Polyadenylation sequences can promote mRNA stability by addition of a polyA tail to the 3' end of the coding sequence and thus, contribute to increased translational efficiency. Recognized polyadenylation sites include an ideal polyA sequence (e.g., ATTAAA, ATTAAA AGTAAA), a bovine growth hormone polyA sequence (BGHpA), a rabbit β-globin polyA sequence (rβgpA), or another suitable heterologous or endogenous polyA sequence known in the art.

If desired, the constructs described herein can include a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler, et al. (1977) Cell 11:223-232) and adenine phosphoribosyltransferase (Lowy, et al. (1990) Cell 22:817-823) genes which can be employed in tk- or aprt-cells, respectively.

In one embodiment, the viral constructs described herein include a long-terminal repeat. The term "long terminal repeat (LTR)" typically refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral vectors described herein can include an entire LTR or can include one or more regions selected from the group consisting of the U3, R, and U5 regions.

In other embodiments, a viral vector can include modified 5' and/or 3' LTRs. Modifications of the 3' LTR are often made to improve the safety of lentiviral or retroviral systems by rendering viruses replication-defective. As used herein, the term "replication-defective" refers to a virus that is not capable of complete, effective replication such that infective virions are not produced (e.g., replication-defective lentiviral progeny). In contrast, the term "replication-competent" refers to wild-type virus or mutant virus that is capable of replication, such that viral replication of the virus is capable of producing infective virions (e.g., replication-competent lentiviral progeny).

The constructs described herein can also be "self-inactivating" (SIN) vectors, e.g., a replication-defective vector in which the right (3') LTR enhancer-promoter region, known as the U3 region, has been modified (e.g., by deletion or substitution) to prevent viral transcription beyond the first round of viral replication. In a further embodiment, the 3' LTR is modified such that the U5 region is replaced, for example, with an ideal poly(A) sequence.

An additional safety enhancement can be provided by replacing the U3 region of the 5' LTR with a heterologous promoter to drive transcription of the viral genome during production of viral particles. Examples of heterologous promoters which can be used include, for example, simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system.

In addition, a viral vector can further contain a packaging sequence (e.g., the psi sequence), a "trans-activation response" genetic element, an "R-region", a reverse transcription site, a FLAP element, an export element, a post-transcriptional regulatory element, and/or a polyadenylation site, among others. One of ordinary skill in the art will recognize the use of such elements and can incorporate them into the design of the vectors as described herein, when desired.

In one embodiment, the construct can further contain at least one element directing the efficient termination and polyadenylation of the heterologous nucleic acid transcripts to increase heterologous gene expression. Transcription termination signals are generally found downstream of the polyadenylation signal. The term "polyA site" or "polyA sequence" as used herein denotes a DNA sequence which directs both the termination and polyadenylation of the nascent RNA transcript by RNA polymerase II. Efficient polyadenylation of the recombinant transcript is desirable as transcripts lacking a poly A tail are unstable and are rapidly degraded. Illustrative examples of polyA signals that can be used in a vector include an ideal polyA sequence (e.g., AATAAA, ATTAAA AGTAAA), a bovine growth hormone polyA sequence (BGHpA), a rabbit β-globin polyA sequence (rβgpA), or another suitable heterologous or endogenous polyA sequence known in the art.

The constructs described herein, when used for gene therapy, can permit expression of a therapeutic agent. A therapeutic agent can be a bioactive protein, a therapeutic protein, a dominant negative mutant, an RNA interference agent, or an miRNA. In one embodiment, the sequence encoding the therapeutic agent is included in a nucleic acid cassette.

The term "nucleic acid cassette" as used herein refers to genetic sequences within the construct which can express an RNA, and subsequently a protein of interest. The nucleic acid cassette is positionally and sequentially oriented within the construct such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a construct, e.g., it has restriction endonuclease sites at each end. In one embodiment, the nucleic acid cassette contains the sequence of a therapeutic gene used to treat disease. The cassette can be removed and inserted into a plasmid or viral vector as a single unit.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are known by those of skill in the art. A retroviral/lentiviral transfer vector can be introduced into a packaging cell line, via transfection, transduction or infection, to generate a producer cell or cell line. The packaging vectors can be introduced into human cells or cell lines by standard methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene can be linked physically to genes encoding by the packaging vector, e.g., by TRES or self-cleaving viral peptides.

Viral envelope proteins (env) determine the range of host cells which can ultimately be infected and transformed by recombinant retroviruses generated from the cell lines. In the case of lentiviruses, such as HIV-1, HIV-2, SIV, FIV and EIV, the env proteins include gp41 and gp120. Preferably, the viral env proteins expressed by packaging cells are encoded on a separate vector from the viral gag and pol genes, as has been previously described.

Illustrative examples of retroviral-derived env genes which can be employed in the vectors and constructs described herein include, but are not limited to: MLV envelopes, 10A1 envelope, BAEV, FeLV-B, RD114, SSAV, Ebola, Sendai, FPV (Fowl plague virus), and influenza virus envelopes. Similarly, genes encoding envelopes from RNA viruses (e.g., RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Birnaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BLV, EBV, CAEV, SNV, ChTLV, STLV, MPMV, SMRV, RAV, FuSV, MH2, AEV, AMV, CT10, EIAV.

In other embodiments, envelope proteins for pseudotyping a virus as useful for vectors or constructs described herein include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpes viruses such as Herpes simplex virus types 1 and 2, varicella zoster, cytomegalovirus, Epstein-Bar virus (EBV), human herpes viruses (HHV), human herpes virus type 6 and 8, Human immunodeficiency virus (HIV), papilloma virus, murine gamma herpes virus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, and any encephalitis causing virus.

In one embodiment, the vector tropism can be modified by expression of an antibody or antigen binding fragment on the surface of the vector particle.

The use of gene therapy constructs in humans is limited by their toxicity, particularly the tendency to produce genotoxicity from the activation of cellular oncogenes by the enhancers present in constructs. Such genotoxicity is evidenced by, for example, the appearance of hematopoietic malignancies in humans treated with gene therapy vectors, and, for example, an increased number of tumors in experimental animals administered viral vectors. While genotoxicity at any level is generally undesirable, the incidence of animals with tumors associated with genotoxicity of the constructs described herein is reduced by at least 50%, at least 75%, at least 80%, at least 90%, at least 95%, at least 98%, at least 99% or more as compared to a construct lacking the genomic insulator element(s) but otherwise identical. In some embodiments, the incidence of tumors associated with genotoxicity of the constructs described herein is reduced by at least 1-fold, at least 2-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 200-fold or more compared to a construct lacking the genomic insulator element(s) but otherwise identical.

Genotoxicity can be determined with various in vitro and in vivo methods including measuring the number or extent of tumors associated with construct administration. In one embodiment, genotoxicity is determined using a tumor transplant genotoxicity assay. In this assay, a cell line transduced with a construct, e.g, a retroviral vector, is transplanted into mice and the number of tumors or rates of tumor free survival are determined in the mice. This assay allows quantification of genotoxic effects by assessing, e.g., rates of tumor free survival or overall rate of tumor formation.

As indicated, the construct of this invention is of use a method for the treatment of disease, in particular a disease to be treated with a lymphocyte (e.g., a T cell or B cell) transduced or transformed with a construct described herein. For the purposes of this invention, the terms "treat" "treatment" "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced.

Alternatively, treatment is "effective" if the progression of a disease is reduced or halted. That is, "treatment" includes not just the improvement of symptoms or markers, but can also include a cessation or at least slowing of progress or worsening of symptoms that would be expected in absence of treatment. Beneficial or desired clinical results include, but are not limited to, alleviation of one or more symptom(s) of a given disease or disorder, diminishment of extent of disease, stabilized disease (i.e., not worsening), delay or slowing of progression of the disease, amelioration or palliation of the disease state, and remission (whether partial or total). The term "treatment" of a disease also includes providing at least partial relief from the symptoms or side-effects of the disease (including palliative treatment).

In one embodiment, as used herein, the term "prevention" or "preventing" when used in the context of a subject refers to stopping, hindering, and/or slowing the development of a given disease or disorder.

As used herein, the term "therapeutically effective amount" means that amount necessary, at least partly, to attain the desired effect, or to delay the onset of, inhibit the progression of, or halt altogether, the onset or progression of the particular disease or disorder being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. In some embodiments, a maximum dose of a therapeutic agent is used, that is, the highest safe dose according to sound medical judgment. It will be understood by those of ordinary skill in the art, however, that a lower dose or tolerable dose that is effective can be administered for medical reasons, psychological reasons or for virtually any other reason.

In one embodiment, a therapeutically effective amount of a pharmaceutical formulation, or a composition described herein for a method of treating a given disease or disorder is an amount sufficient to reduce the level of at least one symptom of the disease or disorder as compared to the level in the absence of the compound, the combination of compounds, the pharmaceutical composition/formulation of the composition. In other embodiments, the amount of the composition administered is preferably safe and sufficient to treat, delay the development of disease, and/or delay onset of the disease. In some embodiments, the amount can thus cure or result in amelioration of the symptoms of the disease, slow the course of the disease, slow or inhibit a symptom of the disease, or slow or inhibit the establishment or development of secondary symptoms associated with the disease. While effective treatment need not necessarily initiate complete regression of the disease, such effect would be effective treatment. The effective amount of a given therapeutic agent will vary with factors such as the nature of the agent, the route of administration, the size and species of the animal to receive the therapeutic agent, and the purpose of the administration. Thus, it is not possible or prudent to specify an exact "therapeutically effective amount." However, for any given case, an appropriate "effective amount" can be determined by a skilled artisan according to established methods in the art using only routine experimentation.

Provided herein are constructs that are useful for treating and preventing a variety of different diseases and/or disorders in a subject. In one embodiment, the composition is a pharmaceutical composition. The composition can include a therapeutically or prophylactically effective amount of a construct encoding a polynucleotide or therapeutic agent.

The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions. Formulations suitable for parenteral administration can be formulated, for example, for intravenous, intramuscular, intradermal, intraperitoneal, and subcutaneous routes. Carriers can include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions.

Therapeutic compositions contain a physiologically tolerable carrier together with the constructs described herein, dissolved or dispersed therein as an active ingredient. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmaceutical composition that contains active ingredients dissolved or dispersed therein is understood in the art and need not be limited based on formulation. Typically, such compositions are prepared as injectable either as liquid solutions or suspensions; however, solid forms suitable for solution, or suspension in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition for use with the methods described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Examples of such additional liquid phases are glycerin, vegetable oils such as cottonseed oil, and water-oil emulsions. The amount of a construct to be administered herein that will be effective in the treatment of a particular disorder or condition will depend on the nature of the disorder or condition, the expression of the therapeutic agent, and can be determined by standard clinical techniques.

While any suitable carrier known to those of ordinary skill in the art can be employed in the pharmaceutical composition, the type of carrier will vary depending on the mode of administration. Compositions for use as described herein can be formulated for any appropriate manner of administration, including for example, topical, oral, nasal, intravenous, intracranial, intraperitoneal, subcutaneous or intramuscular administration. For parenteral administration, such as intramuscular or subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) can also be employed as carriers for the pharmaceutical compositions. Suitable biodegradable microspheres are disclosed, for example, in U.S. Pat. Nos. 4,897,268 and 5,075,109. Such compositions can also include buffers (e.g., neutral-buffered saline or phosphate-buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions as described herein can be formulated as a lyophilizate. Compositions can also be encapsulated within liposomes. The compositions described herein can be administered as part of a sustained-release formulation (i.e., a formulation such as a capsule or sponge that affects a slow release of the constructs following administration). Such formulations can generally be prepared using well-known technology and administered by, for example, oral, rectal or subcutaneous implantation, or by implantation at the desired target site. Sustained-release formulations can contain a vector, polypeptide, polynucleotide dispersed in a carrier matrix and/or contained within a reservoir surrounded by a rate controlling membrane. Carriers for use within such formulations are biocompatible, and can also be biodegradable; preferably the formulation provides a relatively constant level of active component release. The amount of active compound contained within a sustained release formulation depends upon the site of implantation, the rate and expected duration of release and the nature of the condition to be treated or prevented.

Treatment includes prophylaxis and therapy. Prophylaxis or treatment can be accomplished by a single direct injection at a single time point or multiple time points. Administration can also be nearly simultaneous to multiple sites. Patients or subjects include mammals, such as human, bovine, equine, canine, feline, porcine, and ovine animals as well as other veterinary subjects. Preferably, the patients or subjects are human.

In one aspect, the methods described herein provide a method for treating a disease or disorder in a subject. In one embodiment, the subject can be a mammal. In another embodiment, the mammal can be a human, although the approach is effective with respect to all mammals. The method includes administering to the subject an effective amount of a construct as described herein, e.g., in pharmaceutical composition.

The dosage range for the composition depends upon the potency, the expression level of the therapeutic agent and includes amounts large enough to produce the desired effect, e.g., reduction in at least one symptom of the disease to be treated. The dosage should not be so large as to cause unacceptable adverse side effects. Generally, the dosage will vary with the type of inhibitor expressed from the vector (e.g., an antibody or fragment, small molecule, siRNA, etc.) or activator (e.g., recombinant polypeptide, peptide, peptidomimetic, small molecule, etc.), and with the age, condition, and sex of the patient. The dosage can be determined by one of skill in the art and can also be adjusted by the individual physician in the event of any complication. Typically, the dosage of the therapeutic agent and/or the vector composition ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 μg/kg body weight to 30 μg/kg body weight.

In some embodiments, the construct is a viral vector administered at a multiplicity of infection (MOI) of at least 5, at least 10, at least 20, at least 30, at least 40, at least 50, at least 100, at least 200, at least 500 or more.

In other embodiments, the construct is a viral vector administered at a titer of at least $1\times10^5$, $1\times10^6$, $1\times10^7$, $1\times10^8$, $1\times10^9$, $1\times10^{10}$, $1\times10^{11}$, $1\times10^{12}$ or more.

Repeated administration can be performed as necessary to maintain therapeutic efficacy.

A therapeutically effective amount is an amount of a vector or expressed therapeutic agent that is sufficient to produce a statistically significant, measurable change in at least one symptom of a disease. Alternatively, a therapeutically effective amount is an amount of an agent that is sufficient to produce a statistically significant, measurable change in the expression level of a biomarker associated with the disease in the subject. Such effective amounts can be gauged in clinical trials as well as animal studies for a given agent.

The constructs can be administered directly to a particular site (e.g., intramuscular injection, intravenous, into a specific organ) or can be administered orally. It is also contemplated herein that the agents can also be delivered intravenously (by bolus or continuous infusion), by inhalation, intranasally, intraperitoneally, intramuscularly, subcutaneously, intracavity, and can be delivered by peristaltic means, if desired, or by other means known by those skilled in the art. The agent can be administered systemically, if so desired. Alternatively, the construct can be used in ex vivo gene therapy, wherein cells are transduced or engineered with the construct and subsequently infused into a patient to treat disease.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

The efficacy of a given treatment for a disease can be determined by the skilled clinician. However, a treatment is considered "effective treatment," as the term is used herein, if any one or all of the signs or symptoms of the disease to be treated is/are altered in a beneficial manner, other clinically accepted symptoms or markers of disease are improved, or even ameliorated, e.g., by at least 10% following treatment with a construct as described herein. Efficacy can also be measured by failure of an individual to worsen as assessed by stabilization of the disease, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of the disease; or (2) relieving the disease, e.g., causing regression of symptoms; and (3) preventing or reducing the likelihood of the development of the disease or preventing secondary issues associated with the disease.

In certain aspects, the subject being treated with a construct of the invention has been diagnosed with a condition selected from the group of a primary immunodeficiency, haemoglobinopathy or inborn error of metabolism. In certain embodiments, the subject has been diagnosed with a condition selected from the group consisting of Severe Combined Immune Deficiency (SCID), Combined Immune Deficiency (CID), adenosine deaminase deficiency, X-linked adeno-leukodystrophy, Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCK 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia (e.g., β-thalassemia, thalassemia major, thalassemia intermedia, α-thalassemia), sickle cell disease, Mucopolysaccharidosis, Sphingolipidoses, and Osteopetrosis.

What is claimed is:

1. A construct comprising at least one copy of a genomic insulator element having a core sequence selected from the group of CACTGCCCTCCAGTGGCCA (SEQ ID NO:1), CAGCGCCACCTGCAGGCCA (SEQ ID NO:2), CTTCCAGCAGGAGGAGGCA (SEQ ID NO:3), TGGCCGCTAGAGGGCACGC (SEQ ID NO: 4), AAGCACCATCTACTGGTCT (SEQ ID NO:5), CTGCCGCCAGATGGCGCTC (SEQ ID NO: 6), TCAGCACTAGATGGCACCC (SEQ ID NO:7), GAGTGACACCTAGTGGCCC (SEQ ID NO:8), CAGCGCCATCTGGGGGCCG (SEQ ID NO: 9), TCGCCAGTAGGGGGCGCAA (SEQ ID NO:10), TGCTGCCCCCTGGTGGCCA (SEQ ID NO: 11), TGCTGCTCCCTTATGGCCA (SEQ ID NO:12), AGGCCACCAGATGGCATTG (SEQ ID NO: 13), CTGCCACGAGGGGGCGGCA (SEQ ID NO: 14), TTGCGCCCCCTGCTGGCGA (SEQ ID NO:15), CGTCGCCACCTTCTGGTAA (SEQ ID NO: 16), CAGTGCCCTCTGGTGGTAG (SEQ ID NO: 17), TTATGCCCCCTGCAGGACA (SEQ ID NO:18), CGCCCAGAAGGTGGCGGCA (SEQ ID NO:19), and CACTGCCCCCTAGTGGACC (SEQ ID NO:20), wherein the construct is a viral vector, transgene cassette, or transposon system, wherein the genomic insulator element comprises a sequence selected from the group of SEQ ID NO: 21, SEQ ID NO: 22, SEQ ID NO:23, SEQ ID NO:24, SEQ ID NO: 25, SEQ ID NO: 26, SEQ ID NO:27, SEQ ID NO:28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO:39 and SEQ ID NO: 40.

2. The construct of claim 1, wherein the viral vector is a retroviral vector.

3. The construct of claim 2, wherein the retroviral vector is a lentiviral vector.

4. The construct of claim 1, wherein the construct is a gene therapy construct.

5. The construct of claim 1 further comprising a therapeutic agent, optionally wherein the therapeutic agent comprises a gene of interest a protein, a dominant negative mutant, an RNA interference agent, or an miRNA.

6. A host cell comprising the construct of claim 1.

7. The host cell of claim 6, wherein said host cell is a lymphocyte.

8. A pharmaceutical composition comprising the construct of claim 1 and a pharmaceutically acceptable carrier.

9. A method for treating a disease comprising administering a construct of claim 5, wherein the therapeutic agent mediates treatment of the disease.

10. The method of claim 9, wherein the therapeutic agent comprises a protein, a dominant negative mutant, an RNA interference agent, or an miRNA.

11. The method of claim 9, wherein the disease is a primary immunodeficiency, haemoglobinopathy or inborn error of metabolism.

* * * * *